(12) United States Patent
Brown et al.

(10) Patent No.: US 6,306,854 B1
(45) Date of Patent: Oct. 23, 2001

(54) CHEMICAL COMPOUNDS

(75) Inventors: Peter Jonathan Brown, Durham, NC (US); James Mood Chapman, Jr., Columbia, NC (US); Jeffrey Alan Oplinger, Durham, NC (US); Ludwig William Stuart, Durham, NC (US); Timothy Mark Willson, Durham, NC (US); Zhengdong Wu, Malvern, PA (US)

(73) Assignee: Glaxosmithkline, Research Triangle Park, NC (US)

( * ) Notice: Subject to any disclaimer, the term of this patent is extended or adjusted under 35 U.S.C. 154(b) by 0 days.

(21) Appl. No.: 09/806,890

(22) PCT Filed: Oct. 15, 1999

(86) PCT No.: PCT/GB99/03420

§ 371 Date: Apr. 16, 2001

§ 102(e) Date: Apr. 16, 2001

(87) PCT Pub. No.: WO00/23407

PCT Pub. Date: Apr. 27, 2000

(30) Foreign Application Priority Data

Oct. 16, 1998 (GB) .................................................. 9822473

(51) Int. Cl.[7] ...................... A61K 31/5375; A61P 31/04; C07D 295/14
(52) U.S. Cl. ...................... 514/237.8; 544/159; 562/431
(58) Field of Search ............................ 544/159; 562/431; 514/237.8

(56) References Cited

FOREIGN PATENT DOCUMENTS

WO95 18533 A    7/1995  (WO).
WO98 43081 A   10/1998  (WO).

OTHER PUBLICATIONS

Guerre–Millo et al, *Chemical Abstracts*, vol. 133, No. 202, 854, 2000.*
P.J. Brown, et al. "A Ureido–Thiobutyric Acid(GW9578)", J. Med. Chem., vol. 42, No. 19, Apr. 9, 1999, pp. 3785–3788.

* cited by examiner

*Primary Examiner*—Robert W. Ramsuer
(74) *Attorney, Agent, or Firm*—Robert H. Brink

(57) ABSTRACT

Novel compounds of Formula (1) and esters, salts, and physiologically functional derivatives thereof are disclosed. Methods for preparing and using the compounds are also disclosed. Many of these compounds are selective activators of PPAR alpha. The compounds are particularly useful for treating obesity.

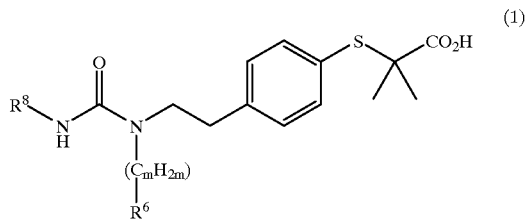

(1)

9 Claims, No Drawings

CHEMICAL COMPOUNDS

This application is filed pursuant to 35 USC §371 as a U.S. National Phase Application No. PCT/GB99/03420 filed Oct. 15, 1999, which claims priority to GB Application No. 9822473.6, filed Oct. 16, 1998.

FIELD OF THE INVENTION

The present invention relates to certain novel PPAR alpha activating compounds, processes for their preparation, pharmaceutical compositions containing the compounds, and uses of the compounds as therapeutic agents.

Obesity can be described as a state of excessive accumulation of body fat, and is widely considered to be a major public health problem. Treatment of obesity remains a problem.

Certain fibrate compounds are described in WO92/10468. Such compounds are said to be useful in the prophylaxis and treatment of atherosclerosis.

PCT publication WO95/18533 describes methods of identifying activators and antagonists of peroxisome proliferator activated receptor ("PPAR") and activators of retinoic acid receptor gamma. The disclosure discusses treating obesity.

BRIEF DESCRIPTION OF THE INVENTION

Briefly, in one aspect, the present invention provides compounds of Formula (1) and esters, salts, and physiologically functional derivatives thereof

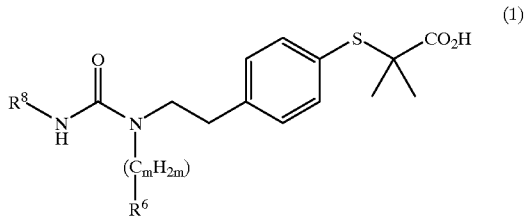

(1)

wherein m is from 0 to 20, $R^6$ is selected from the group consisting of hydrogen and

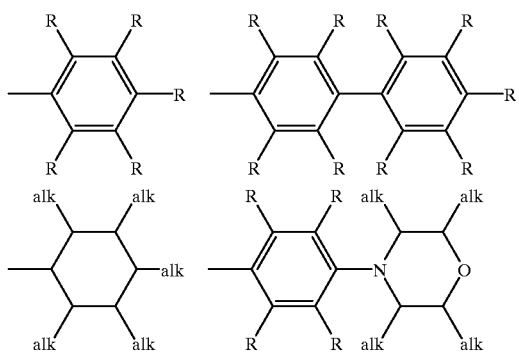

and $R^8$ is selected from the group consisting of

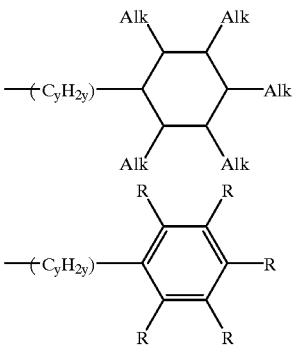

where y is 0, 1, or 2, each alk is independently hydrogen or alkyl group containing 1 to 6 carbon atoms, each R group is independently hydrogen, halogen, cyano, —$NO_2$, phenyl, straight or branched alkyl or fluoroalkyl containing 1 to 6 carbon atoms and which can contain hetero atoms such as nitrogen, oxygen, or sulfur and which can contain functional groups such as ketone or ester, cycloalkyl containing 3 to 7 carbon atoms, or two R groups bonded to adjacent carbon atoms can, together with the carbon atoms to which they are bonded, form an aliphatic or aromatic ring or multi ring system, and where each depicted ring has no more than 3 alk groups or R groups that are not hydrogen. Preferably, the compounds of Formula (1) are PPAR alpha activating compounds.

The compounds of Formula (1) are generally PPAR alpha activating compounds, and therefore are useful in the treatment of a PPAR alpha mediated disease, risk factor, or condition, in particular, obesity and dyslipidemia. Therefore, in another aspect of the invention there is provided a method of treating a PPAR alpha mediated disease, risk factor, or condition, in particular obesity and dyslipidemia, comprising administering to an individual in need thereof a therapeutically effective amount of a PPAR alpha activating compound of Formula (1). The invention further provides the use of a PPAR alpha activating compound of Formula (1) for the manufacture of a medicament for the treatment of a PPAR alpha mediated disease, risk factor, or condition, in particular obesity and dyslipidemia.

The invention further provides compounds of Formula (1) for use in therapy, and pharmaceutical compositions comprising a compound of Formula (1).

The invention also provides methods for preparing the compounds and pharmaceutical compositions of the invention.

As used herein, unless otherwise indicated, the term alkyl or words containing the terms such as fluoroalkyl, can be either straight chain or branched chain. For example, a 3-carbon alkyl group can be either n-propyl or i-propyl.

DETAILED DESCRIPTION OF THE INVENTION

Preferably, the compounds of Formula (1) are PPAR alpha activating compounds. More preferable compounds are those that, in addition to being PPAR alpha activating compounds, are selective activators of PPAR alpha. By "PPAR activating compound", or "PPAR activator", or the like, is meant those compounds which achieve 50% activation of human PPAR ("hPPAR") alpha (in the Transfection assay described below) at concentrations of $10^{-5}$ M or less, as exemplified in the working examples. By selective, is meant those compounds which selectively activate PPAR alpha over PPAR gamma such that the ratio $$\frac{EC_{50} \ PPAR \ Gamma}{EC_{50} \ PPAR \ Alpha}$$

is at least 10, as exemplified in the working examples. Most preferred are those compounds such that this ratio is at least 100.

Preferably, each $R^6$ and $R^8$ has no more than 2 R groups and no more than 2 alk groups that are other than hydrogen. Most preferably, all R groups and all alk groups are hydrogen.

Particularly preferred compounds are those where y is 0, m is from 0 to 6, and each alk and each R group is hydrogen.

Examples of suitable compounds of Formula (1) are 2-(4-(2-(1-(4-Biphenylethyl)-3-cyclohexylureido)ethyl) phenylthio)-2-methylpropionic acid 2-(4-(2-(1-(2-(4-Morpholinophenyl)ethyl)-3-cyclohexylureido)ethyl)phenylthio)-2-methylpropionic acid 2-(4-(2-(1-(Cyclohexanebutyl)-3-cyclohexylureido) ethyl)phenylthio)-2-methylpropionic acid 2-(4-(2-(1-Heptyl-3-(2,4-difluorophenyl)ureido)ethyl) phenylthio)-2-methylpropionic acid 2-(4-(2-(1-(2-Chloro4-(2-trifluoromethylphenyl) phenylmethyl)-3-(cyclohexyl)ureido)ethyl) phenylthio)-2-methylpropionic acid and esters, salts, and physiologically functional derivatives thereof.

Particularly preferred compounds of Formula (1) are 2-(4-(2-(1-(4-Biphenylethyl)-3-cyclohexylureido)ethyl) phenylthio)-2-methylpropionic acid 2-(4-(2-(1-(2-(4-Morpholinophenyl)ethyl)-3-cyclohexylureido)ethyl)phenylthio)-2-methylpropionic acid 2-(4-(2-(1-(Cyclohexanebutyl)-3-cyclohexylureido) ethyl)phenylthio)-2-methylpropionic acid and esters, salts, and physiologically functional derivatives thereof.

The compounds of this invention can be prepared in a variety of ways. For example, the compounds of Formula (1) can be prepared by reacting the compounds of Formulas (2), (3), and (4), $$R^8\text{---}NCO \quad (2)$$

$$\begin{array}{c} R^6(C_{m-1}H_{2m-2}) \\ | \\ CO_2H \end{array} \quad (3)$$

(4)

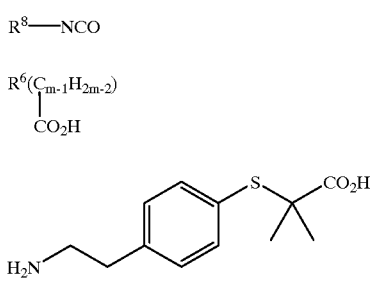

to give compounds of the invention of Formula (1) wherein $R^6$, $R^8$, and m are as defined above. Synthetic routes will also be illustrated in the working examples below.

The compounds of the present invention may be utilized in the form of a pharmaceutically acceptable salt or solvate thereof. Preferred salts of compounds of Formula (1) are those that are physiologically acceptable. However, non-physiologically acceptable salts are within the scope of the present invention for use as intermediates in the preparation of the compounds of the invention and their physiologically acceptable salts and physiologically functional derivatives.

The "physiologically functional derivatives" referred to herein are compounds which are converted in vivo to a compound of Formula (1) or one of its physiologically acceptable salts.

Many of the compounds of this invention will contain one or more stereocenters. The present invention includes all possible stereoisomers, tautomers, and geometric isomers of the compounds, including optically enriched compositions as well as the racemic mixtures. When an enantiomerically enriched composition is desired, it may be obtained either by resolution of the final product or by stereospecific synthesis from either isomerically pure starting material or any convenient intermediate. Resolution of the final product, an intermediate, or a starting material may be effected by any suitable method. See, for example, Stereochemistry of Carbon Compounds, by E. L. Eliel (Mcgraw Hill, 1962) and Tables of Resolving Agents, by S. H. Wilen.

Reference to "treatment" includes prophylaxis as well as the treatment of established of established diseases or symptoms. Moreover, it will be appreciated that the amount of a compound of the invention required for use in treatment will vary with the nature of the condition being treated and the age and the condition of the patient and will be ultimately at the discretion of that attendant physician or veterinarian.

PPAR alpha, gamma, and delta are recognized subtypes of PPARs. The PPARs are known to bind to their target genes as heterodimers with RXR. The present invention provides PPAR alpha activating compounds for use in the treatment of obesity, dyslipidemia, and other PPAR alpha mediated diseases, conditions, or risk factors. More particularly, the present invention provides PPAR alpha activators useful in the treatment of Alzheimer's disease, atherosclerosis, obesity, inflammation, cancer, psoriasis, pancreatitis, and various disease risk factors. Most preferably the PPAR alpha activators are selective. Disease risk factors may include dyslipidemia, hypertriglyceridemia, hyperlidipemia, and hypercholesterolemia. See, for example, K. M. Anderson, et al., *An Updated Coronary Risk Profile*, AHA Medical/Scientific Statement Science Advisory, vol. 83, pp 356–362 (1991), W. P. Castilli, *The Triglyceride Issue: A View From Farmingham*, Am. Heart J., vol. 112, pp 432–437 (1986), M. Austin, *Plasma Triglyceride and Coronary Heart Disease*, Arteriosclerosis and Thrombosis, vol.11, pp 2–14 (1991), and J. J. Genest, et al., *Prevalence of Familial Lipoprotein Disorders in Patients With Premature Coronary Artery Disease*, vol. 85, pp 2025–2033 (1992). PPAR Alpha agonists have been shown to have antitumor activity. See, for example, Samid et al, Biochem. Pharmacol. (1996) 52, 659–667. PPAR Alpha agonists have been shown to have antiinflammatory activity. See, for example, Wahli et. al., Nature (1996) 384, 3943. PPAR Alpha agonists have been shown to have antiatherosclerotic activity. See, for example, Staels et. al., Nature (1998) p790.

A recognized clinical and epidemiological measure for the classification of obesity is the Body Mass Index (BMI) which is defined as weight in kilograms divided by the square of height in meters. Typically, a BMI of 25–30 is considered as overweight and >30 as obese. Treatment according to the present invention generally refers to a lowering of BMI to less than about 29 to 31. It will however be appreciated by persons skilled in the art that obesity is inherently difficult to classify, and that the cut-off point for the definition of obesity is necessarily arbitrary, in part because body fatness is a continuum. However, in general terms treatment according to the present invention desirably prevents or alleviates obesity to an extent whereby there is no longer a significant health risk to the patient.

The amount of a PPAR alpha activator which is required to achieve the desired biological effect will, of course, depend on a number of factors, for example the mode of administration and the precise clinical condition of the recipient. In general, the daily dose will be in the range of 0.01 mg–1 g/kg, typically 0.1–100mg/kg. An intravenous dose may, for example, be in the range of 0.001 mg to 0.1 g/kg, typically 0.01mg to 10 mg/kg, which may conveniently be administered as an infusion of from 0.1 µg to 1 mg, per minute. Infusion fluids suitable for this purpose may contain, for example, from 0.01 µg to 0.1 mg, per milliliter. Unit doses may contain, for example, from 0.01 µg to 0.1 g of a PPAR alpha activator. Thus ampoules for injection may contain, for example, from 0.01 µg to 0.1 g and orally administrable unit dose formulations, such as tablets or capsules, may contain, for example, from 0.1 mg to 1 g.

A compound of this invention may be employed in the treatment of a disease or condition as the compound per se, but is preferably presented with an acceptable carrier in the form of a pharmaceutical formulation. The carrier must, of course, be acceptable in the sense of being compatible with the other ingredients of the formulation and must not be deleterious to the recipient. The carrier may be a solid or a liquid, or both, and is preferably formulated with the activator as a unit-dose formulation, for example, a tablet, which may contain from 0.05% to 95% by weight of the activator.

The formulations include those suitable for oral, rectal, topical, buccal (e.g. sub-lingual) and parenteral (e.g. subcutaneous, intramuscular, intradermal or intravenous) administration.

Formulations suitable for oral administration may be presented in discrete units, such as capsules, cachets, lozenges or tablets, each containing a predetermined amount of a PPAR alpha activator; as a powder or granules; as a solution or a suspension in an aqueous or non-aqueous liquid; or as an oil-in-water or water-in-oil emulsion. In general, the formulations are prepared by uniformly and intimately admixing the active PPAR alpha activator with a liquid or finely divided solid carrier, or both, and then, if necessary, shaping the product. For example, a tablet may be prepared by compressing or molding a powder or granules of the PPAR alpha activator optionally with one or more accessory ingredients. Compressed tablets may be prepared by compressing, in a suitable machine, the compound in a free-flowing form, such as a powder or granules optionally mixed with a binder, lubricant, inert diluent and/or surface active/dispersing agent(s). Molded tablets may be made by molding, in a suitable machine, the powdered compound moistened with an inert liquid diluent.

Formulations suitable for buccal (sub-lingual) administration include lozenges comprising a PPAR alpha activator in a flavored base, usually sucrose and acacia or tragacanth, and pastilles comprising the activator in an inert base such as gelatin and glycerin or sucrose and acacia.

Formulations of the present invention suitable for parenteral administration conveniently comprise sterile aqueous preparations of a PPAR alpha activator, preferably isotonic with the blood of the intended recipient. These preparations are preferably administered intravenously, although administration may also be effected by means of subcutaneous, intramuscular, or intradermal injection. Such preparations may conveniently be prepared by admixing the activator with water and rendering the resulting solution sterile and isotonic with the blood. Injectable compositions according to the invention will generally contain from 0.1 to 5% w/w of the activator.

Formulations suitable for rectal administration are preferably presented as unit-dose suppositories. These may be prepared by admixing a PPAR alpha activator with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include Vaseline, lanolin, polyethylene glycols, alcohols, and combinations of two or more thereof. The PPAR alpha activator is generally present at a concentration of from 0.1 to 15% w/w of the composition, for example, from 0.5 to 2%.

EXPERIMENTAL

The following examples are given in illustration of, but not limitation of, the invention. Each of the following Examples of the invention showed 50% activation of hPPAR alpha at concentration of $10^{-5}$M or less and are therefore, activators of hPPAR alpha. It is possible to prepare a large variety of the compounds of Formula (1) using standard solid phase synthetic methods such as those illustrated in the following working examples. The prepared compounds can then readily be screened for activity and selectivity using the Transfection assay described below. By using these techniques, one can readily determine which compounds of Formula (1) are activators of PPAR alpha and which compounds of Formula (1) are selective activators of PPAR alpha. In addition, the highly efficient Binding assay described below can be used to quickly pre-screen large numbers of compounds and those compounds that are shown to bind can then be screened for activity and selectivity.

INTERMEDIATE 1 t-Butyl 2-(4-bromophenylthio)-2-methylpropionate

A mixture of 4-bromothiophenol (100 g; 0.53 mole) and potassium hydroxide (29.5 g; 0.53 mole) in ethanol (1000 mL) was stirred until all material had dissolved. t-Butyl 2-bromoisobutyrate (117.6 g; 0.53 mole) was added dropwise over 30 min, keeping the temperature below 55° C. The resulting mixture was heated at reflux for 1 h, then cooled to 23° C. The precipitate (KBr) was removed by filtration and the solvent evaporated. The residue was partitioned between water (1000 mL) and methylene chloride (500 mL) and the organic layer was separated, dried ($Na_2SO_4$) and evaporated to afford a white solid. Crystallization from hexane gave a white solid (119.85 g; 68%).

$^1$H-NMR (CDCl$_3$) δ 7.41 (d, 2H, J=7.5 Hz), 7.35 (d, 2H, J=7.5 Hz), 1.40 (s, 15H).

INTERMEDIATE 2 t-Butyl 2-(4-(2-phthalimidoethenyl)phenylthio)-2-methylpropionate

A mixture of Intermediate 1 (50 g; 150 mmole), N-vinylphthalimide (27.2 g; 157 mmole), palladium acetate (1.68 g; 7.5 mmole), tri-o-tolylphosphine (3.07 g; 15 mmole) and triethylamine (42 mL) in a sealed tube was gently heated until all solids had dissolved then heated at 110° C. for 15 h. The solvent was evaporated and the residue partitioned between 2N HCl (300 mL) and ethyl acetate (300 mL) and filtered through celite. The organic layer was separated and the aqueous layer was extracted with ethyl acetate (100 mL). The combined organic layers were washed with brine (100 mL), dried (MgSO$_4$) and evaporated. The residue was purified by chromatography using EtOAc-Hexane-CH$_2$Cl$_2$ as eluent to afford a yellow solid 43.14 g; 68%).

$^1$H-NMR (CDCl$_3$) δ 7.90 (dd, 2H, J=3.3 Hz, J'=5.4 Hz), 7.76 (dd, 2H, J=3.3 Hz, J'=5.4 Hz), 7.64 (d, 1H, J=15.3 Hz), 7.48 (d, 2H, J=8.4 Hz), 7.41 (d, 2H, J=8.4 Hz), 7.37 (d, 1H, J=15.3 Hz), 1.45 (s, 6H), 1.43 (s, 9H).

INTERMEDIATE 3 t-Butyl 2-(4-(2-phthalimidoethyl)phenylthio)-2-methylpropionate

A solution of Intermediate 2 (43.1 g; 100 mmole) in THF (600 mL) was added to a suspension of Wilkinson's Catalyst (tris(triphenylphosphine)rhodium chloride) (5 g) in ethanol (100 mL) and the mixture stirred under an atmosphere of hydrogen (20 psi) for 5 h. The solvent was evaporated and the residue was purified by chromatography using EtOAc-Hexane-CH$_2$Cl$_2$ as eluent to afford a light brown solid (37 g).

$^1$H-NMR (CDCl$_3$) δ 7.82 (dd, 2H, J=3.4 Hz, J'=5.6 Hz), 7.70 (dd, 2H, J=3.4 Hz, J'=5.6 Hz), 7.41 (d, 2H, J=8.0 Hz), 7.20 (d, 2H, J=8.0 Hz), 3.91 (t, 2H, J=7.8 Hz), 2.98 (t, 2H, J=7.8 Hz), 1.40 (s, 9H), 1.39 (s, 6H).

INTERMEDIATE 4 t-Butyl 2-(4-(2-aminoethyl)phenylthio)-2-methylpropionate

A solution of Intermediate 3 (29.3 g; 69 mmole) in ethanol (500 mL) was treated with hydrazine hydrate (20 g; 350 mmole) and the resulting mixture heated at reflux for 1 h and left to stand at 23° C. for 15 h. The resultant solid was removed by filtration, the solvent evaporated, and the residue partitioned between 1N NaOH (150 mL) and ether (1300 mL). The organic layer was separated and washed with 1N NaOH (100 mL) and brine, dried (MgSO$_4$) and evaporated to afford an oil (19.9 g; 97%). $^1$H-NMR (CDCl$_3$) δ 7.42 (d, 2H, J=8.0 Hz), 7.14 (d, 2H, J=8.0 Hz), 2.98 (br, 2H), 2.78 (t, 2H, J=7.0 Hz), 2.51 (br, 2H), 1.41 (s, 15H).

INTERMEDIATE 5 t-Butyl 2-(4-(2-fluoren-9-ylmethyloxycarbonylaminoethyl)phenylthio)-2-methylpropionate A solution of Intermediate 4 (37.9 g; 130 mmole) in dioxane (100 mL) was treated with a solution of sodium carbonate (13.6 g; 130 mmole) in water (200 mL) followed by a slurry of Fmoc-OSu (43.3 g; 130 mmole) in dioxane (100 mL) and the mixture was stirred at 23° C. for 5 h. The organic solvent was evaporated and the residue was acidified with 1N HCl. The organic material was extracted with CH$_2$Cl$_2$ (2×200 mL) and the combined organic layers were dried (Na$_2$SO$_4$) and evaporated. The residue was purified by chromatography using 15 then 20% EtOAc-Hexane as eluent to afford a gum (49.3 g; 74%). $^1$H-NMR (CDCl$_3$) δ 7.77 (d, 2H, J=7.6 Hz), 7.57 (d, 2H, J=7.6 Hz), 7.44 (d, 2H, J=8.0 Hz), 7.31 (t, 2H, J=7.2 Hz), 7.13 (d, 2H, J=8.0 Hz), 4.77 (m, 1H), 4.42 (d, 2H, J=6.8 Hz), 4.21 (t, 1H, J=6.8 Hz), 3.44 (q, 2H, J=6.4 Hz), 2.81 (t, 2H, J=6.8 Hz), 1.44 (s, 6H), 1.42 (s, 9H).

INTERMEDIATE 6

2-(4-(2-Fluoren-9-ylmethyloxycarbonylamino)ethyl)phenylthio)-2-methylpropionic Acid A solution of Intermediate 5 (27.1 g; 52 mmole) in TFA (135 mL) and CH$_2$Cl$_2$ (135 mL) was stirred at 23° C. for 5 h. The solvent was evaporated and the residue dissolved in CH$_2$Cl$_2$ (200 mL) and washed with water (3×150 mL) and brine (2×100 mL), dried (MgSO$_4$) and evaporated to afford a low melting solid (22.9 g; 95%). $^1$H-NMR (CDCl$_3$; complicated by rotamers) δ 9.25 (br, 1H), 7.76 (d, 2H, J=7.2 Hz), 7.56 (d, 2H, J=7.2 Hz), 7.46 (d, 2H, J=7.6 Hz), 7.39 (t, 2H, J=7.2 Hz), 7.30 (t, 2H, J=7.2 Hz), 7.13 (d, 2H, J=7.6 Hz), 4.88 (br, 0.6H), 4.54 (br, 0.4H), 4.40 (d, 1.2H, J=6.8 Hz), 4.19 (t, 0.8H, J=6.8 Hz), 3.43 (q, 1.2H, J=6.4 Hz), 3.17 (br, 0.8H), 2.80 (t, 1.2H, J=7.2 Hz), 2.53 (br, 0.8 Hz), 1.50 (s, 6H). Analysis Found: C, 68.97; H, 6.04; N, 2.95. C$_{27}$H$_{27}$NO$_4$S o 0.5H$_2$O Requires: C, 68.91; H, 6.00; N, 2.98%.

INTERMEDIATE 7

Intermediate 6 Loaded onto SASRIN® Resin

A solution of Intermediate 6 (9.66g, 20.93 mmole), 4-dimethylaminopyridine (256 mg; 2.093 mmole) and diisopropylcarbodiimide (2.635 g; 20.88 mmole) in CH$_2$Cl$_2$ (40 mL) was stirred at 23° C. for 10 min. SASRIN® resin (4.7 g; 0.89 mmol/g; 4.186 mmole) was added and the resulting solution stirred at 23° C. for 1.5 h. The resin was filtered and washed with CH$_2$Cl$_2$ (3×100 mL) then suspended in CH$_2$Cl$_2$ (40 mL) and treated with diisopropylethylamine (7 mL) and isovaleric anhydride (4 mL). After stirring at 23° C. for 1 h, the resin was filtered and washed with CH2Cl$_2$ (3×75 mL), DMF (3×75 mL), MeOH (3×75 mL) then CH$_2$Cl$_2$ (3×75 mL) and dried in vacuum. Resin loading was determined by standard FMOC analysis (0.3–0.43 mmole/g).

INTERMEDIATE 8 t-Butyl N-(Cyclohexylbutanoyl)-2-(4-(2-aminoethyl)phenylthio)-2-methylpropionate A solution of Intermediate 4 (77 g; 260.6 mmole) and cyclohexanebutanoic acid (66.55 g; 390.9 mmole) in CH$_2$Cl$_2$ (500 mL) was treated with HOBT o H$_2$O (20 g; 130.7 mmole) and diisopropylcarbodiimide (112.6 g; 521.2 mmole) and the resulting solution stirred at 23° C. for 15 h. The solution was washed with saturated NaHCO$_3$ solution, 1N HCl and brine and the organic layer was dried (Na$_2$SO$_4$) and evaporated. The residue was purified by chromatography using 20% EtOAc-Hexane as eluent to afford a white solid (100.7 g; 86%). $^1$H-NMR (CDCl$_3$) δ 7.42 (d, 2H, J=8.0 Hz), 7.13 (d, 2H, J=8.0 Hz), 5.87 (br s, 1H), 3.49 (q, 2H, J=6.8 Hz), 2.81 (t, 2H, J=7.2 Hz), 2.12 (t, 2H, J=7.6 Hz), 1.73–1.52 (m, 7H), 1.41 (s, 15H), 1.26–1.07 (m, 6H), 0.84 (m, 2H).

INTERMEDIATE 9 t-Butyl 2-(4-(2-(Cyclohexylbutylamino)ethyl)phenylthio)-2-methylpropionate

A solution of Intermediate 8 (5 g; 5.92 mmole) in THF (50 mL) was treated with a 1M solution of borane in THF (40 mL; 40 mmole) and the mixture allowed to stand at 23° C. for 15 h. Excess borane was destroyed by the careful addition of n-butanol (20 mL) and the resulting solution heated under reflux for 2h. The solvent was evaporated the residue was purified by chromatography using EtOAc then 10% MeOH-EtOAc as eluent to afford an oil (3.78 g; 66%). $^1$H-NMR (CDCl$_3$) δ 7.41 (d, 2H, J=8.0 Hz), 7.14 (d, 2H, J=8.0 Hz), 2.84 (m, 4H), 2.61 (t, 2H, J=7.2 Hz), 2.05 (br, 1H), 1.65 (m, 6H), 1.41 (s, 15H), 1.33–1.07 (m, 6H), 0.82 (m, 2H).

INTERMEDIATE 10 t-Butyl 2-(4-(2-(1-(Cyclohexanebutyl)-3-cyclohexylureido)ethyl)phenylthio)-2-methylpropionate A solution of Intermediate 9 (5 g; 11.5 mmole) and cyclohexylisocyanate (1.73 g; 13.8 mmole) in $CH_2Cl_2$ (50 mL) was allowed to stand at 23° C. for 18 h. The solvent was evaporated and the residue purified by chromatography using 10% EtOAc-Hexane as eluent to afford a white solid (5.3 g; 83%). $^1$H-NMR (CDCl$_3$) δ 7.42 (d, 2H, J=8.1 Hz), 7.15 (d, 2H, J=8.1 Hz), 4.01 (d, 1H, J=7.8 Hz), 3.61 (m, 1H), 3.39 (t, 2H, J=7.5 Hz), 3.03 (t, 2H, J=7.5 Hz), 2.83 (t, 2H, J=7.5 Hz), 1.90 (m, 2H), 1.74–1.52 (m, 8H), 1.42 (s, 15H), 1.50–0.96 (m, 15H), 0.85 (m, 2H).

EXAMPLE 1

2-(4-(2-(1-(Cyclohexanebutyl)-3-cyclohexylureido)ethyl)phenylthio)-2-methylpropionic Acid A solution of Intermediate 9 (5g; 8.96 mmole) in $CH_2Cl_2$ (40 mL) and TFA (40 mL) was allowed to stand at 23° C. for 4 h. The solvent was evaporated to afford a semi-solid, which was purified by chromatography using 5–20% MeOH-$CH_2Cl_2$ as eluent to afford a white solid (3.7 g; 82%). $^1$H-NMR (CDCl$_3$) δ 9.05 (br, 1H), 7.44 (d, 2H, J=8.0 Hz), 7.15 (d, 2H, J=8.0 Hz), 4.28 (br, 1 H), 3.63 (br s, 1H), 3.41 (t, 2H, J=7.4 Hz), 3.01 (t, 2H, J=7.6 Hz), 2.83 (t, 2H, J=7.2 Hz), 1.89 (m, 2H), 1.72–1.52 (m, 8H), 1.42 (s, 6H), 1.52–0.95 (m, 15H), 0.85 (m, 2H).

The following Example was prepared using the procedures outlined for the preparation of Example 1.

EXAMPLE 2

2-(4-(2-(1-(4-Biphenylethyl)-3-cyclohexylureido)ethyl)phenylthio)-2-methylpropionic Acid General Method
General solid phase synthesis method for preparation of 2-(4-(2-Substituted ureido)ethyl)phenylthio)-2-methylpropionic acids 40 mg of Intermediate 7 (0.43 mmol/g) was suspended in 1 mL of 20% piperidine in DMF for 30 min. The solution was drained and the resin was washed with DMF, $CH_2Cl_2$, MeOH, $CH_2Cl_2$, THF, and DMF. A solution of a carboxylic acid (1M in DMF, 0.17 mL), HOBT (1M in DMF, 0.17 mL), and DIC (1M in DMF, 0.17 mL) were added. The suspension was mixed and then stood at room temperature for 2 h. The solution was drained and the resin was washed with DMF, $CH_2Cl_2$, MeOH, $CH_2Cl_2$, and THF. A solution of $BH_3OTHF$ (1 M in THF, 0.52 mL) was added. The suspension was mixed and then stood at room temperature for 18 h. The solution was drained and the resin was washed with THF, $CH_2Cl_2$, DMF, MeOH, $CH_2Cl_2$ and DMF. A solution of an isocyanate (1M in DMF, 0.52 mL) was added. The suspension was mixed and then stood at room temperature for 18 h. The solution was drained and the resin was washed with DMF, $CH_2Cl_2$, MeOH, $CH_2Cl_2$, THF, and $CH_2Cl_2$. The resulting resin was suspended in 1 mL of 10% TFA in $CH_2Cl_2$ for 30 min. The solution was filtered and the filtrate evaporated to yield the 2-(4-(2-(Substituted ureido)ethyl) phenylthio)-2-methylpropionic acid.

Using the General Method, the following example was synthesized from Intermediate 7.

EXAMPLE 3

2-(4-(2-(1-(2-Chloro-4-(2-trifluoromethylphenyl)phenylmethyl)-3-(cyclohexyl)ureido)ethyl)phenylthio)-2-methylpropionic Acid

INTERMEDIATE 11

2-(4-(2-(Phenylmethyloxycarbonylamino)ethyl)phenoxy)-2-methylbutanoic Acid

A solution of 4-(2-(phenylmethyloxycarbonylamino)ethyl)phenol (5.74 g; 21.16 mmole) in 2-butanone (17 mL) and chloroform (6 g) was added dropwise to a mixture of sodium hydroxide (9.0 g; 225 mmole) and 2-butanone (67 mL) whilst keeping the reaction temperature below 30° C. The mixture was allowed to stir at 30° C. for 4 h. Ether (100 mL) was added and the resultant solid was collected by filtration and washed with ether (100 mL). The solid was dissolved in water (70 mL) and any residual ether removed by evaporation. 1N Hydrochloric acid was added to adjust the pH to 1, and the resulting oil was extracted with dichloromethane (3×50 mL). The combined extracts were dried ($Na_2SO_4$) and evaporated to afford a yellow oil (3.82 g; 49%).

$^1$H-NMR (CDCl$_3$) δ 7.26 (s, 5H), 7.09 (d, 2H, J=7.9 Hz), 6.88 (d, 2H, J=8.4 Hz), 5.09 (s, 2H), 4.75 (br s, 1H), 3.42–3.44 (m, 2H), 2.75 (t, 2H, J=6.7 Hz), 1.92–2.00 (m, 2H), 1.47 (s, 3H), 1.04 (t, 3H, J=2.6 Hz). Mass spectrometry $ES^-$, m/e $(M+H)^+$=372.

INTERMEDIATE 12

Methyl 2-(4-(2-(phenylmethyloxycarbonylamino)ethyl)phenoxy)-2-methyl butyrate A solution of Intermediate 11 (2.0 g; 5.38 mmole) in dimethylformamide (12 mL) was treated with potassium carbonate (2.23 g; 16.14 mmole) and methyl iodide (1.54 g; 10.76 mmole) and the resulting mixture stirred at 23° C. for 2 h. The mixture was filtered and the solid collected was washed with ethyl acetate (70 mL). The filtrate was washed with brine (4×50 mL), dried ($Na_2SO_4$) and evaporated. The residue was purified by chromatography on silica gel using hexane then 33% ethyl acetate-hexane as eluent to afford a colorless oil (1.27 g; 61%).

$^1$H-NMR (DMSO-d$_6$) δ 7.31 (m, 5H), 7.06 (d, 2H, J=8.4 Hz), 6.68 (d, 2H, J=8.4 Hz), 4.98 (s, 2H), 3.67 (s, 3H), 3.15 (m, 2H), 2.62 (t, 2H, J=7.1 Hz), 1.86 (m, 2H), 1.38 (s, 3H), 0.86 (t, 3H, J=7.3 Hz). Mass spectrometry $ES^+$, m/e $(M+Na)^+$=408.

INTERMEDIATE 13

Methyl 2-(4-(2-aminoethyl)phenoxy)-2-methylbutyrateacetate Salt

A solution of Intermediate 12 (1.27 g; 3.29 mmole) in methanol (50 mL) and acetic acid (0.4 g) was treated with 10% palladium on carbon and shaken in a hydrogen atmosphere (50 psi) for 2 h. The catalyst was filtered through celite and the solvent was evaporated to afford a yellow oil in quantitative yield (1.04 g).

$^1$H-NMR (CDCl$_3$): δ 7.06 (d, 2H, J=8.4 Hz), 6.77 (d, 2H, J=8.4 Hz), 6.70 (br s, 2H) 3.76 (s, 3H), 3.02 (br s, 2H), 2.82 (m, 2H), 1.99 (s, 3H), 1.92 (m, 2H), 1.48 (s, 3H), 0.96 (t, 3H, J=7.4 Hz). Mass spectrometry $ES^+$, m/e $(M+H)^+$=252.

INTERMEDIATE 14

Methyl 2-(4-(2-(2,4-dinitrophenylsulfonylamino)ethyl)phenoxy)-2-methyl butyrate A solution of Intermediate 13 (2 g; 6.42 mmole) in $CH_2Cl_2$ (40 mL) was treated with saturated sodium bicarbonate solution and the organic layer was separated. The aqueous layer was extracted with $CH_2Cl_2$ (5×50 mL) and the combined organic layers were dried ($Na_2SO_4$) and evaporated to afford the free base as a yellow oil (1.61 g; 100%). This was dissolved in $CH_2Cl_2$ (40 mL) and treated with pyridine (0.45 g; 5.61 mmole) and 2,4-dinitrophenylsulfonyl chloride (1.5 g; 5.61 mmole), and the mixture was allowed to stir at 23° C. for 3 h. Water (60 mL) was added and the organic layer separated, washed with water (3×40 mL) and saturated sodium bicarbonate (40 mL). The organic layer was dried ($Na_2SO_4$) and evaporated and the residue purified by chromatography using 15–20% EtOAc-Hexane as eluent to afford a light yellow solid (1.38 g; 51%).

$^1$H-NMR (CDCl$_3$): δ 8.63 (d, 1H, J=2.3 Hz), 8.49 (dd, 1H, J=8.4 Hz, J'=2.3 Hz), 8.07 (d, 1H, J=8.4 Hz), 6.89 (d, 2H, J=8.4 Hz), 6.54 (d, 2H, J=8.4 Hz), 5.34 (t, 1H, J=5.3 Hz), 3.78 (s, 3H), 3.48 (q, 2H, J=8.3 Hz), 2.75 (t, 2H, J=6.6 Hz), 1.92 (m, 2H), 1.42 (s, 3H), 0.93 (t, 3H, J=7.5 Hz).

INTERMEDIATE 15

Methyl 2-(4-(2-((2,4-dinitrophenylsulfonyl)(hept-2-en-1-yl))amino)ethyl)phenoxy)-2-methyl butyrate A solution of Intermediate 14 (315 mg; 0.654 mmole) in THF (15 mL) was treated with triphenylphosphine (343 mg; 1.308 mmole), hept-2-en-1-ol (150 mg; 1.308 mmole) and diethylazodicarboxylate (228 mg; 1.308 mmole) and the mixture allowed to stir at 23° C. for 1 h. The solvent was evaporated and the residue purified by chromatography using 10–15% EtOAc-Hexane as eluent to afford a semi-solid (400 mg; >100%). TLC and NMR shows that the desired compound is present along with 1,2-(diethoxycarbonyl)hydrazine.

INTERMEDIATE 16

Methyl 2-(4-(2-(hept-2-en-1-ylamino)ethyl) phenoxy)-2-methyl butanoate

A solution of Intermediate 15 (400 mg; 0.654 mmole) in $CH_2Cl_2$ (5 mL) was treated with triethylamine (132 mg; 1.308 mmole) and mercaptoacetic acid (78 mg; 0.85 mmole) and the mixture was allowed to stir at 23° C. for 1 h. The mixture was diluted with EtOAc (30 mL) and washed with water (3×20 mL) and aqueous sodium bicarbonate (30 mL). The organic layer was dried ($Na_2SO_4$), evaporated and the residue purified by chromatography using 10% EtOAc-Hexane then 50% EtOAc-Hexane then MeOH as eluent to afford an oil (177 mg; 78% from intermediate 24).

$^1$H-NMR (CDCl$_3$): δ 7.06 (d, 2H, J=7.5 Hz), 6.75 (d, 2H, J=7.5 Hz), 5.59 (m, 2H), 3.76 (s, 3H), 3.30 (d, 2H, J=6.3 Hz), 2.87 (m, 4H), 1.96 (m, 4H), 1.47 (s, 3H), 1.28 (m, 5H), 0.96 (t, 3H, J=7.6 Hz), 0.86 (t, 3H, J=6.9 Hz).

INTERMEDIATE 17

Methyl 2-(4-(2-(1-hept-2-enyl-3-(2,4-difluorophenyl)ureido)ethyl)phenoxy)-2-methylbutyrate A solution of Intermediate 16 (157 mg; 0.452 mmole) in methylene chloride (5 mL) was treated with 2,4-difluorophenylisocyanate (140 mg; 0.904 mmole) and the mixture allowed to stand at 23° C. for 18 h. The solvent was evaporated and the residue purified by chromatography on silica gel using 10% then 15% ethyl acetatehexane as eluent to afford a yellow semi-solid (212 mg; 93%). Contaminated with bis-(2,4-difluorophenyl)urea which co-elutes on column.

$^1$H-NMR (CDCl$_3$): δ 8.85 (brs, 1H), 8.02 (m, 1H), 7.09 (d, 2H, J=8.4 Hz), 6.77–6.90 (m, 4H), 5.70 (m, 1H), 5.36 (m, 1H), 3.76 (s, 3H), 3.54 (t, 2H, J=7.3 Hz), 2.84 (t, 2H, J=7.1 Hz), 1.55 (br s, 1H), 1.46 (s, 3H), 1.25–1.35 (m, 5H), 0.96 (t, 3H, J=7.3 Hz), 0.88 (t, 3H, J=7.4 Hz). Mass spectrometry Cl/AP$^+$, m/e (M+H)$^+$=503.

RADIOLIGAND PRECURSOR 2-(4-2-(1-Hept-2-enyl-3-(2,4-difluorophenyl)ureido) ethyl) phenoxy)-2-methylbutanoic Acid A solution of Intermediate 17 (370 mg; 0.736 mmole) in methanol (15 mL) was treated with 1N NaOH (7.5 mL) and the mixture heated under reflux for 2 h. The mixture was acidified with 1N HCl and extracted with ethyl acetate (3×25 mL). The combined organic layers were washed with brine, dried ($Na_2SO_4$) and evaporated. The residue was purified by chromatography on silica gel using 20% ethyl acetatehexane then ethyl acetate as eluent to afford a tan oil (280 mg; 78%).

$^1$H-NMR (CDCl$_3$) δ 7.95–8.09 (m, 1H), 7.14 (d, 2H, J=7.1 Hz), 6.90 (d, 2H, J=7.4 Hz), 6.81 (d, 2H, J=5.2 Hz), 5.66 (m, 1H), 5.37 (m, 1H), 3.56 (t, 2H, J=7.4 Hz), 2.87 (t, 2H, J=7.4 Hz), 2.00 (m, 4H), 1.44 (s, 3H), 1.27 (m, 6H), 1.03 (t, 3H, J=7.3 Hz), 0.88 (t, 3H, J=7.3 Hz). Mass spectrometry ES$^-$, m/e (M+H)$^+$=489.

RADIOLIGAND 2-(4-(2-(2,3-Ditritio-1-heptyl-3-(2,4-difluorophenyl) ureido)ethyl)phenoxy)-2-methylbutanoic Acid A solution of the Radioligand precursor (10 mg) in anhydrous DMF (3.5 mL) was transferred to a reaction vessel containing 10% Pd/C (9.8 mg). The reaction vessel was evacuated and degassed via one freeze-thaw-evacuation cycle and then exposed to tritium gas (10.1 Ci). After 4 h, the mixture was filtered through celite, evaporated and the residue dissolved in acetonitrile. A portion of this solution (0.8 mL, 26.6 mCi) was purified by HPLC (Dynamax C8, 25 min gradient from 4:1 acetonitrile:0.1%TFA to 9:1 acetonitrile: 0.1% TFA, 235 nm). Fractions containing pure material were combined and evaporated under nitrogen. The residue was redissolved in acetonitrile to provide a solution of the title compound (82.0 Ci/mmol, radiochemical purity, 99%).

The above Radioligand was used in the binding assay described below to show that compounds which were active in the transfection assay were also ligands for PPAR Alpha.

COLD RADIOLIGAND 2-(4-(2-(1-Heptyl-3-(2,4-difluorophenyl)ureido) ethyl)phenoxy)-2-methylbutanoic Acid A solution of the Radioligand precursor (10 mg) in anhydrous DMF (3.5 mL) was transferred to a reaction vessel containing 10% Pd/C (9.8 mg). The reaction vessel was evacuated and degassed via one freeze-thaw-evacuation cycle and then exposed to hydrogen gas. After 4 h, the mixture was filtered through celite and evaporated. The residue was purified by chromatography using 2% MeOH/$CH_2Cl_2$ as eluent to afford a gum (7mg).

INTERMEDIATE 18

Tert-butyl-2-[4-(2-(2-(4-morpholinylphenyl)-1-oxoethyl)aminoethyl) phenylthio]-2-methyl propionate To a solution of Intermediate 4 (3.54 g, 12 mmol) and (4-morpholinylphenyl) acetic acid (3.1 g, 14 mmol) in $CH_2Cl_2$ (200 mL) was added 1-(3-dimethyl aminopropyl)-3-ethylcarbodiimide hydrohloride (2.7 g;14 mmol). The mixture was stirred for 4 hr at 23° C. After diluting with $CH_2Cl_2$ (200 mL), the solution was washed twice with water (100 mL), dried ($Na_2SO_4$), evaporated, and the residue purified by silica gel chromatography to yield a light tan-colored solid (4.5 g; 75%). Mass Spectrum (ES$^+$) 499.1 (MH$^+$, 60%), 521.1 (M+Na$^+$, 100%); $^1$H NMR (CDCl$_3$) δ 7.36 (d, 2H, J=8.1 Hz), 7.05 (d, 2H, J=8.6 Hz), 6.99 (d, 2H, J=7.9 Hz), 6.84 (d, 2H, J=8.5 Hz), 5.36 (br s, 1H), 3.87 (t, 4H, J=4.8 Hz), 3.45 (s, 2H), 3.42 (q, 2H, J=6.4 Hz), 3.15 (t, 4H, J=4.8 Hz), 2.72 (t, 2H, J=7.0 Hz), 1.42 (s, 15H).

INTERMEDIATE 19 t-Butyl 2-(4-(2-(1-(2(4-Morpholinophenyl)ethyl)-3-cyclohexylureido)ethyl)phenylthio)-2-methylpropionate To a 0° C. THF (75 mL) solution of Intermediate 18 (3.88 g, 7.78 mmol) was added of 1M BH$_3$.THF complex in THF (54.4 mL; 54.4 mmol). The solution was allowed to stir for 5 h while gradually warming to 23° C. After cooling to 0° C., MeOH (50 mL) was added dropwise and the solution was concentrated to dryness. The resulting oil was refluxed for 30 min with n-butanol (50 mL) in the presence of 4 mL (excess) of cyclohexylisocyanate. Upon cooling and concentration, the crude product was purified by silica gel chromatography using 20%–80% EtOAc in Hexanes as eluent to yield a colorless, viscous oil (2.8 g; 60%). Mass Spectrum (ES$^+$) 610.1 (MH$^+$, 60%), 632.1 (M+Na$^+$, 50%); $^1$H NMR (d$_6$-DMSO) δ 7.33 (d, 2H, J=8.1 Hz), 7.18 (d, 2H, J=7.9 Hz), 7.02 (d, 2H, J=8.6 Hz), 6.82 (d, 2H, J=8.6 Hz), 5.63 (d, 1H, J=7.8 Hz), 3.69 (t, 4H, J=4.5 Hz), 3.4–3.2 (m, 5H plus water peak), 3.00 (t, 4H, J=4.5 Hz), 2.69 (t, 2H, J=7.2 Hz), 2.57 (t, 2H, J=7.2 Hz), 1.65 (m, 4H), 1.53 (d, 1H, J=12.7 Hz), 1.32 (s, 9H), 1.3 (s, 9H), 1.2–1.0 (m, 5H).

EXAMPLE 4

2-(4-(2-(1-(2-(4-Morpholinophenyl)ethyl)-3-cyclohexylureido)ethyl)phenylthio)-2-methylpropionic Acid To a solution of Intermediate 19 (2.75 g, 4.5 mmol) in CH$_2$Cl$_2$ (50 mL) at 0° C. was added 60 mL of 1:1 TFA: CH$_2$Cl$_2$. The solution was stirred for 60 min, then warmed to 23° C. and stirred an additional 60 min. After concentration to dryness, the crude product as a solution in MeOH/CH$_2$Cl$_2$ was neutralized to pH=~7 with NH$_4$OH/MeOH solution. The biphasic mixture was separated, the aqueous phase washed with CH$_2$Cl$_2$ and the combined organics dried (Na$_2$SO$_4$) and concentrated. Silica gel chromatography eluting with CH$_2$Cl$_2$, then 1%–20% MeOH in CH$_2$Cl$_2$ gave a maroon-colored oil. A second flush through a short plug of silica gel with 10% MeOH in 1:1 EtOAc: CH$_2$Cl$_2$ removed most of the color to yield a light tan-colored foamy solid (2.05 g; 82%). Mass Spectrum (ES$^+$) 554.1 (MH$^+$, 100%), 576.1 (M+Na$^+$, 90%); $^1$H NMR (d$_6$-DMSO) δ 7.33 (d, 2H, J=8.0 Hz), 7.18 (d, 2H, J=8.0 Hz), 7.04 (d, 2H, J=8.6 Hz), 6.82 (d, 2H, J=8.2 Hz), 5.63 (d, 1H, J=7.7 Hz), 3.7 (t, 4H, J=4.7 Hz), 3.3 (t, 2H, J=7.6 Hz), 3.23 (t, 2H, J=7.5 Hz), 3.00 (t, 4H, J=4.6 Hz), 2.69 (t, 2H, J=7.5 Hz), 2.58 (t, 2H, J=7.4 Hz), 1.66 (m, 4H), 1.54 (d, 1H, J=12.7 Hz), 1.31 (s, 6H), 1.2–1.0 (m, 5H).

INTERMEDIATE 20 t-Butyl N-Heptanoyl-2-(4-(2-aminoethyl)phenylthio)-2-methylpropionate

A solution of Intermediate 4 (297 mg; 1.006 mmole) and heptanoic acid (196 mg; 1.51 mmole) in CH$_2$Cl$_2$ (7 mL) was treated with HOBToH$_2$O (77 mg; 0.5 mmole) and diisopropylcarbodmide (253 mg; 2.012 mmole) and the resulting solution stirred at 23° C. for 15 h. The solution was washed with saturated NaHCO$_3$ solution, 1N HCl and brine and the organic layer was dried (Na$_2$SO$_4$) and evaporated. The residue was purified by chromatography using 20% EtOAc-Hexane as eluent to afford a gum (241 mg). $^1$H-NMR (CDCl$_3$) δ 7.37 (d, 2H, J=8.0 Hz), 7.07 (d, 2H, J=8.0 Hz), 5.35 (br s, 1H), 3.44 (m, 2H), 2.75 (t, 2H, J=7.0 Hz), 2.28 (t, 1H, J=7.5 Hz), 2.05 (t, 2H, J=7.7 Hz), 1.47–1.59 (m, 3H), 1.35 (m, 13H), 1.19 (m, 6H), 0.8 (m, 3H).

INTERMEDIATE 21 t-Butyl 2-(4-(2-(1-Heptyl-3-(2,4-difluorophenyl)ureido)ethyl)phenylthio)-2-methylpropionate A solution of Intermediate 20 (241 mg; 0.592 mmole) in THF (5 mL) was treated with a 1M solution of borane in THF (4 mL; 4 mmole) and the mixture allowed to stand at 23° C. for 15 h. Excess borane was destroyed by the careful addition of methanol and the resulting solution heated under reflux for 30 min. The solvent was evaporated and the residue was dissolved in CH$_2$Cl$_2$ (5 mL) and treated with 2,4-difluorophenylisocyanate (184 mg; 1.184 mmole) and allowed to stand at 23° C. for 15 h. The mixture was washed with 2N HCl and the organic layer was dried (Na$_2$SO$_4$) and evaporated. The residue was purified by chromatography using EtOAc-Hexane as eluent to afford an oil (270 mg). $^1$H-NMR (CDCl$_3$) δ 8.03 (m, 1H), 7.44 (d, 2H, J=8.2 Hz), 7.18 (d, 2H, J=7.8 Hz), 6.83 (m, 2H), 6.34 (br s, 1H), 3.52 (t, 2H, J=7.5 Hz), 3.19 (t, 2H, J=7.8 Hz), 2.92 (t, 2H, J=7.5 Hz), 1.59 (m, 2H), 1.41 (m, 13H), 1.3 (m, 9H), 0.88 (m, 3H).

EXAMPLE 5

2-(4-(2-(1-Heptyl-3-(2,4-difluorophenyl)ureido)ethyl)phenylthio)-2-methylpropionic Acid A solution of Intermediate 21 (270 mg; 0.506 mmole) in CH$_2$Cl$_2$ (3 mL) and TFA (3 mL) was allowed to stand at 23° C. for 4 h. The solvent was evaporated to afford a semi-solid (240 mg). $^1$H-NMR (CDCl$_3$) δ 7.99 (m, 1H), 7.45 (d, 2H, J=7.8 Hz), 7.20 (d, 2H, J=8.1 Hz), 6.82 (m, 2H), 6.34 (brs, 1H), 3.53 (t, 2H, J=7.5 Hz), 3.16 (t, 2H, J=7.6 Hz), 2.92 (t, 2H, J=7.4 Hz), 2.20 (br, 2H), 1.85 (br, 2H), 1.75–1.52 (m, 4H), 1.42 (s, 6H), 1.45–1.15 (m, 11H), 0.87 (t, 3H, J=6.8 Hz).

Binding Assay.

To generate a bacterial expression plasmid for the ligand binding domain of hPPAR alpha, cDNA encoding the hinge and ligand binding domains of hPPAR alpha (amino acids 167–468) was amplified by polymerase chain reaction and the amplified product inserted in frame into the pGEX-2T plasmid (Pharmacia). The amplified region of hPPAR alpha was sequence confirmed. GST-hPPAR alpha was expressed in BL21(DE3)plysS cells and extracts prepared by freeze-thawing the cells in Bacterial Lysis Buffer (10 mM Tris, pH 8.0, 250 mM KCl, 1 mM DTT, 1% Triton X-100) followed by centrifugation at 40,000×g for 30 minutes. Glycerol was added to the bacterial extracts to a final concentration of 10%. Bacterial extracts were dialyzed extensively against Bacterial Lysis Buffer containing 10% glycerol. Binding assays included 50 μg of bacterial extracts (containing GST-hPPAR alpha), 60 nM Radioligand, and either 10 μM Cold Radioligand (or comparative example) or vehicle alone (0.1% DMSO, final concentration) in buffer containing 10 mM Tris (pH 8.0), 50 mM KCl, 10 mM DTT. Binding reactions were incubated at 4° C. for 2–3 hr. Bound radioactivity was separated from free radioactivity by elution through 1 ml Sephadex G-25 protein desalting columns (Boehringer Mannheim). Bound radioactivity eluted in the column void volume and was quantitated by liquid scintillation counting.

Results (data represent the mean of assays performed in triplicate and are presented as dpm).

| No competitor | 140000 |
|---|---|
| + 10 μM Cold Radioligand | 25000 |
| Specific Binding | 115000 |

Transfection Assay

Plasmids: GAL4-hPPAR alpha chimera and UAS-tk-SPAP reporters. The GAL4-hPPAR alpha and the GAL4-hPPAR gamma expression constructs contain the translation initiation sequence and amino acids 1–76 of the glucocorticoid receptor fused to amino acids 1–147 of the yeast (S.crevisiae) transcription factor GAL4 in the pSG5 expression vector (Stratagene). Amino acids 167–468 of hPPAR alpha or amino acids 195–475 of hPPAR gamma were amplified by polymerase chain reaction (PCR) using vent polymerase (New England Biolabs) and inserted C-terminal to the GAL4 sequences. The UAS-tk-SPAP reporter contain 5 copies of the GAL4 binding site inserted into pG12-tk-SPAP (Berger et al, 1988).

Transfection assay: SPAP reporter. CV-1 cells were plated in DME medium supplemented with 10% delipidated fetal calf serum at a density of $2.4 \times 10^4$ cells per well in a 96-well plate (Costar) 16–24 h before transfection. In general, 8.0 ng of reporter plasmid, 25.0 ng of β-galactosidase expression vector (pCH 110, Pharamacia), and 2.0 ng of GAL4-hPPAR alpha or GAL4-hPPAR gamma expression vector were mixed with carrier DNA (pBluescript, Stratagene) to a total of 80 ng of DNA per well in a volume of 10 ml optiMEM I medium (Life Technologies). To this, a second mix, containing 9.3 ml optiMEM I medium and 0.7 ml of LIPOFECTAMINE™ (Life Technologies), was added. After 30 min. an additional 80 ml of optiMEM I medium were added and the combined mix was then applied to the cells. 16 h later the medium was exchanged to DME medium supplemented with 10% delipidated and heat inactivated fetal calf serum and the test compound at a concentration of $10^{-5}$M. After incubation for 24 h, SPAP activity and β-galactosidase activity were measured by directly adding to the medium 200 ml substrate mix (16 mM o-nitrophenyl β-D-galactopyranoside (Sigma), 120 mM fluorescein diphosphate (Molecular Probes), 0.16% Triton X-100, 160 mM diethanolamine pH9, 44.8mM NaCl, and 0.8 mM $MgCl_2$). Alternatively, alkaline phosphatse and β-galactosidase activities were measured separately using standard protocols. Briefly, cells were lysed by adding 25 ml 0.5% Triton X-100 to the supernatant. To 40 ml cell lysate, 200 ml β-galactosidase substrate reagent (36mM o-nitrophenyl β-D-galactopyranoside, 1.25mM $MgCl_2$, 2.8mM NaCl, 4.4M β-mercaptoethanol) or 200 ml alkaline phosphatase substrate reagent (2.5 mM p-nitrophenyl phosphate, 0.5 mM $MgCl_2$, 28 mM NaCl, 1 M diethanolamine pH 9.85) were added and incubated for 1 h. Alkaline phosphatase activity was expressed as percent maximal induction obtained for reference compound BRL49653, normalized to β-galactosidase activity which served as internal control standard for transfection efficiency.

References; see, for example, Berger, J., et al., (1988), Gene 66, 1–10.

Each of the five Examples showed 50% activation of hPPAR alpha at concentrations of $10^{-5}$ M or less. These five examples also selectively activate PPAR alpha over PPAR gamma such that the activity ratio, as explained above, is at least 10. Examples 1, 2, and 3 had activity ratios greater than 100.

The following rodent data was produced using Example 5. The purpose of the experiment is to demonstrate that activators of PPAR alpha are useful for the treatment of obesity, and dyslipidemia.

Diet-Induced Model of Dyslipidemia

Zucker lean male rats and Zucker fa/fa female rats were randomized into 3 treatment groups. The randomization was based on serum triglyceride concentration after three months on the TEKLAD high fat diet. Dosing with Example 5 or the appropriate vehicle, by oral gavage, began after 4 months of high fat feeding. Plasma glucose, lactate, serum insulin and lipid concentrations were obtained weekly, beginning on day 7 through 48 after the initiation of therapy. Metabolic data from each treatment group was collected weekly. Dexascan determinations of body mass composition obtained after 4 months on the high fat diet served as baseline. Changes in body mass composition due to therapy were determined by repeat measurements at the end of the study.

Treatment Group A Vehicle dosed twice a day (approximately 8 am and 4 pm).

Treatment Group B Example 5 (0.1 mg/kg) dosed twice a day.

Treatment Group C Example 5 (0.3 mg/kg) dosed twice a day.

The results are summarized in the following two tables.

| | Males (n = 4) | | | |
|---|---|---|---|---|
| | | After 4 months on high-fat diet Control | Week 1 | Week 4 | Week 7 |
| | Group | | Drug Treatment | | |
| Triglycerides (mg/dL) | Vehicle | 788 | 718 | 741 | 725 |
| | 0.1 mg/kg | 828 | 460 | 467 | 584 |
| | 0.3 mg/kg | 926 | 527 | 174 | 219 |
| Cholesterol (mg/dL) | Vehicle | 227 | 191 | 224 | 215 |
| | 0.1 mg/kg | 221 | 138 | 189 | 148 |
| | 0.3 mg/kg | 235 | 138 | 174 | 151 |
| NEFA (m Eq/L) | Vehicle | 0.67 | 0.85 | 0.65 | 0.60 |
| | 0.1 mg/kg | 0.72 | 0.73 | 0.57 | 0.58 |
| | 0.3 mg/kg | 0.72 | 0.69 | 0.47 | 0.46 |
| Body Weight (g) | Vehicle | 621 | 610 | 610 | 632 |
| | 0.1 mg/kg | 636 | 617 | 592 | 597 |
| | 0.3 mg/kg | 639 | 608 | 577 | 565 |

| | Females (n = 4) | | | |
|---|---|---|---|---|
| | | After 4 months on high-fat diet Control | Week 1 | Week 4 | Week 7 |
| | Group | | Drug Treatment | | |
| Triglycerides (mg/dL) | Vehicle | 8222 | 5357 | 10414 | 5465 |
| | 0.1 mg/kg | 9310 | 2717 | 3913 | 2627 |
| | 0.3 mg/kg | 9190 | 1627 | 687 | 538 |
| Cholesterol (mg/dL) | Vehicle | 1670 | 1186 | 1319 | 923 |
| | 0.1 mg/kg | 1648 | 610 | 733 | 632 |
| | 0.3 mg/kg | 1908 | 350 | 404 | 422 |
| NEFA (m Eq/L) | Vehicle | 11.10 | 6.78 | 2.79 | 3.77 |
| | 0.1 mg/kg | 11.15 | 2.47 | 1.32 | 1.75 |
| | 0.3 mg/kg | 13.06 | 1.45 | 0.59 | 0.53 |

| | | Females (n = 4) | | | |
|---|---|---|---|---|---|
| | Group | After 4 months on high-fat diet Control | Week 1 | Week 4 Drug Treatment | Week 7 |
| Body Weight (g) | Vehicle | 649 | 684 | 700 | 706 |
| | 0.1 mg/kg | 665 | 721 | 723 | 710 |
| | 0.3 mg/kg | 645 | 673 | 643 | 582 |

What is claimed is:

1. A compound of Formula (1), or a salt thereof

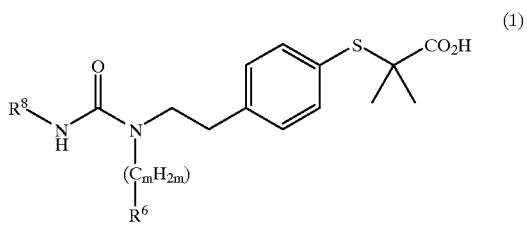

(1)

wherein m is from 0 to 20, $R^6$ is selected from the group consisting of hydrogen and

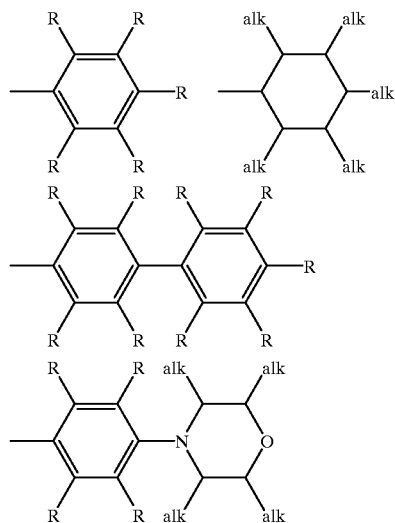

and $R^8$ is selected from the group consisting of

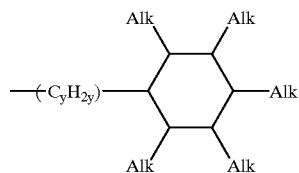

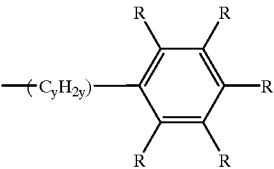

where y is 0, 1, or 2, each alk is independently hydrogen or alkyl group containing 1 to 6 carbon atoms, each R group is independently hydrogen, halogen, cyano, —$NO_2$, phenyl, straight or branched alkyl or fluoroalkyl containing 1 to 6 carbon atoms and which can contain hetero atoms such as nitrogen, oxygen, or sulfur and which can contain functional groups such as ketone or ester, cycloalkyl containing 3 to 7 carbon atoms, or two R groups bonded to adjacent carbon atoms can, together with the carbon atoms to which they are bonded, form an aliphatic or aromatic ring or multi ring system, and where each depicted ring has no more than 3 alk groups.

2. The compound of claim 1 wherein each $R^6$ and each $R^8$ has no more than 2 R groups and no more than 2 alk groups that are other than hydrogen.

3. The compound of claim 1 wherein y is 0, m is from 0 to 6, and each alk and each R group is hydrogen.

4. The compound of claim 1 wherein said compound is 2-(4-(2-(1-(4-Biphenylethyl)-3-cyclohexylureido)ethyl)phenylthio)-2-methylpropionic acid 2-(4-(2-(1-(2-(4-Morpholinophenyl)ethyl)-3-cyclohexylureido)ethyl)phenylthio)-2-methylpropionic acid 2-(4-(2-(1-(Cyclohexanebutyl)-3-cyclohexylureido)ethyl)phenylthio)-2-methylpropionic acid 2-(4-(2-(1-Heptyl-3-(2,4-difluorophenyl)ureido)ethyl)phenylthio)-2-methylpropionic acid 2-(4-(2-(1-(2-Chloro-4-(2-trifluoromethylphenyl)phenylmethyl)-3-(cyclohexyl)ureido)ethyl)phenylthio)-2-methylpropionic acid or a salt thereof.

5. The compound of claim 1 wherein said compound is 2-(4-(2-(1-(4-Biphenylethyl)-3-cyclohexylureido)ethyl)phenylthio)-2-methylpropionic acid 2-(4-(2-(1-(2-(4-Morpholinophenyl)ethyl)-3-cyclohexylureido)ethyl)phenylthio)-2-methylpropionic acid 2-(4-(2-(1-(Cyclohexanebutyl)-3-cyclohexylureido)ethyl)phenylthio)-2-methylpropionic acid or a salt thereof.

6. A pharmaceutical composition comprising a compound according to claim 1.

7. A method for treating obesity or dyslipidemia comprising administration of a compound of claim 1.

8. A method for treating a PPAR alpha mediated disease, risk factor, or condition comprising administering an effective amount of a compound of claim 1.

9. The method of claim 8 wherein said disease, risk factor, or condition is, or is associated with Alzheimer's disease, obesity, dyslipidemia, atherosclerosis, or diabetes.

* * * * *

UNITED STATES PATENT AND TRADEMARK OFFICE
CERTIFICATE OF CORRECTION

PATENT NO.    : 6,306,854 B1
DATED         : October 23, 2001
INVENTOR(S)   : Brown et al.

It is certified that error appears in the above-identified patent and that said Letters Patent is hereby corrected as shown below:

<u>Title page,</u>
Reads, [75] Inventors (second inventor) "James Mood Chapman, Jr., Columbia, NC (US)" should be -- James Mood Chapman, Jr., Columbia, SC (US) --

Reads, [73] Assignee: "Glaxosmithkline, Research Triangle Park, NC, (US)" should be -- University of South Carolina, Columbia, SC and SmithKline Beecham Corporation, Philadelphia, PA --

Signed and Sealed this

Fourteenth Day of May, 2002

*Attest:*

JAMES E. ROGAN
*Attesting Officer*            *Director of the United States Patent and Trademark Office*